United States Patent [19]

Crosby, Jr.

[11] Patent Number: 4,555,932

[45] Date of Patent: Dec. 3, 1985

[54] METHOD AND APPARATUS FOR ASSAYING THE PURITY OF A GAS

[75] Inventor: Edward L. Crosby, Jr., West Melbourne, Fla.

[73] Assignee: RCA Corporation, Princeton, N.J.

[21] Appl. No.: 576,913

[22] Filed: Feb. 3, 1984

[51] Int. Cl.[4] ........................................... G01N 29/02
[52] U.S. Cl. ...................................................... 73/24
[58] Field of Search ............................................ 73/24

[56] References Cited

U.S. PATENT DOCUMENTS

| | | | |
|---|---|---|---|
| 2,568,277 | 9/1951 | Eltgroth | 73/24 |
| 2,874,564 | 2/1959 | Martin et al. | 73/24 |
| 3,120,750 | 2/1964 | Root, III | 73/24 |
| 3,343,403 | 9/1967 | Romani et al. | 73/24 |
| 3,353,400 | 11/1967 | Schafft | 73/24 |
| 3,381,520 | 5/1968 | Bourquard et al. | 73/24 |
| 3,468,157 | 9/1969 | Burk et al. | 73/24 |
| 3,762,197 | 10/1973 | Roof et al. | 73/24 |
| 3,981,176 | 9/1976 | Jacobs | 73/24 |
| 4,003,242 | 1/1977 | Houben et al. | 73/24 |
| 4,220,040 | 9/1980 | Noguchi et al. | 73/24 |
| 4,280,183 | 7/1981 | Santi | 73/24 |

FOREIGN PATENT DOCUMENTS 3009566  9/1981  Fed. Rep. of Germany .......... 73/24

OTHER PUBLICATIONS

"Gas Meter", GOW-MAC Instrument Company, Bulletin SB-20.
"Model 20-600 Portable Gas Analyzer", GOW-MAC Instrument Company, Bulletin 20-600.
"Thermal Conductivity Gas Analyzer", GOW-MAC Instrument Company, Bulletin SB-GA.

Primary Examiner—Bernard Nozick
Attorney, Agent, or Firm—Joseph S. Tripoli; George E. Haas; William Squire

[57] ABSTRACT

Apparatus for assaying the purity of a gas, e.g., helium, includes an acoustic signal generating transducer in a chamber containing the gas under test. In one embodiment, a microphone spaced a given distance from the transducer senses the propagated acoustic signal. A regenerative circuit creates a pulse train of acoustic signals in the chamber having a pulse repetition rate which is a function of the gas purity. In a second embodiment a continuous acoustic signal is propagated in the chamber containing two spaced microphones. The frequency of the acoustic signal is adjusted until the signals received by the microphones are either in phase or 180° out of phase. A peak or null detector detects when the desired phase relationship occurs as the signal frequency is adjusted. The gas purity is then computed from the observed pulse repetition rate or the observed frequency of the in-phase or 180° out-of-phase condition. Temperature compensation is provided for both embodiments.

13 Claims, 3 Drawing Figures

METHOD AND APPARATUS FOR ASSAYING THE PURITY OF A GAS

This invention relates to assaying the purity of a gas containing an unknown amount of contaminants.

Sonic apparatuses for analyzing gases are well known, and may include an acoustical chamber containing a gas under test, transducer means for providing an acoustical signal in the chamber, and a sensor device or devices in the chamber for sensing the transmitted acoustical signal. Several different approaches are taken with these prior art apparatuses. One approach is to detect the phase difference between the propagated acoustic wave at several points in the acoustic chamber or between the propagated wave and the acoustic signal prior to propagation. A second approach propagates an acoustic signal in a resonant chamber, and detects the phase differences of the propagated signal at different positions in the chamber. A third approach employs whistle-type devices which resonate at a given frequency for a given gas and for a given gas chamber configuration, and ascertaining that resonant frequency. Other approaches are also utilized using two chamber systems and reference gases for comparison purposes, among others.

The sending and/or receiving transducers in sonic gas analyzing or detecting systems usually have a fixed spacing. The gas under test is evaluated by determining the velocity of the audio signal in that gas. The most convenient way of determining the sonic velocity in a gas is to measure the phase of the propagated audio signal.

Consider an acoustic signal of a known frequency, propagated in a path in a gas under test in which path are two receptor transducers, such as microphones, separated by a distance d. The propagation of the acoustic signal in the gas has the general relation $V=f\lambda$, where V is the acoustic signal propagation velocity in the gas, f is the acoustic signal frequency in the gas, and $\lambda$ is the acoustic signal wavelength in the gas. The microphones, upon detecting the respective incident acoustic signals, generate corresponding output signals which are in phase when the distance d equals the acoustic signal wavelength.

If one gas is substituted for another gas, the propagation velocity, V, of the substituted gas would differ. This would change the output signals' phase difference from zero to some other value, since for a fixed microphone's spacing $\lambda$ is a function of only the propagation velocity, which is a fundamental characteristic of each gas species derived from its thermodynamic behavior. Measurement of the resulting phase difference between the output signals of the two microphones, then, by simple calculation provides the value of V. The value of V is used to evaluate the gas under test using a graph or look-up table.

However, phase measurement or phase comparison are relatively difficult operations if accuracy and stability to a tolerance of ±1° phase difference or better are desired. The principle problems in phase measurement are related to the amplitude sensitivity of, and waveform purity required by phase detectors. The discussion of phase detection is a complex problem beyond the scope of the present disclosure. An objective standard of the complexity of such measuring systems is given by conventional commercial instrumentation employing phase detection circuitry, which, to provide an accuracy of a fraction of a degree, usually require relatively complex, costly circuitry and a controlled laboratory environment.

Further, many phase measuring systems, in addition to being plagued with the complex problems of phase measurement involving stability, thermal considerations, and amplitude sensitivity are also not readily adaptable for portable field applications. In some cases, it is desired to measure or analyze a gas outside the laboratory environment. For example, in one case, in a remote geographic area, a gas, such as helium, is employed in aerostats, lighter-than-air vehicles. The measurement and analysis of the purity of helium in that case represents a practical problem which present instrumentation does not solve. Here, gas samples need be transported over relatively long distances for analysis by laboratory instrumentation and may require a week or more before laboratory results reach the field installation. This is simply not an acceptable procedure.

Also, even present sophisticated phase measuring systems do not provide the extreme accuracy required for measuring purity of gases employed in such aerostat vehicles, due to the critical level of purity required for such gases. For example, it is required in these aerostat systems to know, within a fraction of a percent, the purity of the involved gases. Because present phase measuring systems require thermal and environmental stability, field applications, where such controls are not generally easily attainable, make the application of such instrumentation relatively difficult.

While a large number of so-called gas analyzing systems employing acoustic signals are known, the systems are generally deficient due to the technique of employing phase measurement, as discussed above, and, therefore, do not readily provide a true quantitative analysis of a gas under test, much less measure the purity of the gas to a practical degree.

An example of some prior art systems include U.S. Pat. No. 2,874,564, issued to Martin et al. which describes a phase comparison of the amplified signals produced by the microphones in a resonant system. In Martin et al., the differentiation of the resultant sine wave of the system produce spikes which, though sharp, have a time jitter as a result of amplitude and waveform instability of the original sinusoid wave, in addition to minute irregularities producing gross errors in the resulting so-called analysis. The switching and integrating circuitry disclosed is also unsuitable for analogous reasons.

U.S. Pat. No. 3,468,157 issued to Burk et al. employs an acoustical chamber, an oscillator for providing a signal to the acoustical chamber, and mixer means for mixing the oscillated signal passed through the acoustical chamber with the original oscillated signal. The mixer output signals, whose phase angles may differ, are provided as inputs to a phase angle null detector. This system uses heterodyne techniques to permit the use of high frequencies and a delay line which, in effect, provides an offset so that the phase change can be observed at lower frequencies. These features provide high effective gain at the expense of stability and, hence, accuracy.

In view of the above, I have observed, that, in practice, there is a sparsity of commercially available or generally known portable instruments for providing an accurate, repeatable stable analysis of gases and, in particular, helium. Present laboratory instruments in use include a mass spectrometer and a gas chromatograph using molecular sieves. Both are relatively unsuitable for field use; the latter is very fragile.

An apparatus and method of assaying the purity of a gas containing an unknown amount of contaminants which meet the above objectives and according to the present invention, comprises propagating an oscillating signal in the gas between two points spaced apart a given distance. The oscillating signal has a repetition rate in a range of frequencies which is a function of the gas purity. The repetition rate of the signal is determined and from the determined repetition rate and the given distance, the velocity of the signal propagating between the two points is determined. Then the purity of the gas is derived from the determined velocity.

By determining the repetition rate of the signal, which repetition rate can have any value in a range of values which corresponds to a given gas composition and deriving the purity of the gas from the determined repetition rate and the given distance, the stability and accuracy problems of phase comparison systems is avoided. Further, instrumentation embodying the present invention is relatively simple to construct and operate and is portable for field use by unskilled personnel.

In more detail, the approach of the present invention is one which recognizes that a direct measurement of the difference in phase between two signals is relatively complex, difficult to obtain, and prone to inaccuracies and instability. The approach is to determine a value of a parameter of an acoustic signal propagating in a gas under test which is not prone to inaccuracies, instability, and can be determined with relatively simple circuitry. That parameter is the frequency of an acoustic signal or, more particularly, the repetition rate of an oscillating acoustic signal propagating in the gas under test. As will be shown, it is a much simpler task to ascertain that repetition rate than the phase differences as employed in prior art systems, as discussed in more detail in the introductory portion.

In one approach of the present invention, an acoustic pulse is propagated in the gas under test. That signal is propagated over a known distance in a given time interval which interval is a function of the gas composition. That signal is processed to regeneratively produce subsequent acoustic pulses in the gas under test. The repetition rate of the pulses, as will be shown, is a function of the velocity of the pulses in the gas media over the known distance. By merely measuring that pulse repetition rate, which is a simple and relatively error-free task, the purity of the gas can be derived to a high degree of accuracy. Temperature measurement of the gas can provide information for temperature correcting the purity measurement of the gas to provide further accuracy and stability employing a simple, low-cost apparatus.

A second approach continuously propagates an acoustic signal in the gas under test. Two receivers spaced a known distance apart generate, in response to receipt of the propagated acoustic signal, two output signals whose phase relationship is a function of the propagation velocity and, thus, the composition of the gas under test. Because the receivers are spaced a known distance apart and at different distances from the acoustic signal source, there always exists some frequency of the acoustic signal at which the phase of the received signals will either be in time coincidence or 180° out of phase. Therefore, the frequency of the acoustic signal is adjusted until the phases of the signals received by the two receivers are either in phase or 180° out of phase, which is a simple task to observe. To observe such phase relationships, a null or peak detector detects the phase coincidence or 180° out-of-phase information. The frequency of the signal propagated in the gas medium is noted and the percent purity derived. Temperature compensation provides a corrected computation for a given gas under test. In this way the repetition frequency of the propagated oscillating signal in the gas can be readily determined and provide a stable, accurate analysis of the relative purity of the gas under test.

Figure 1:
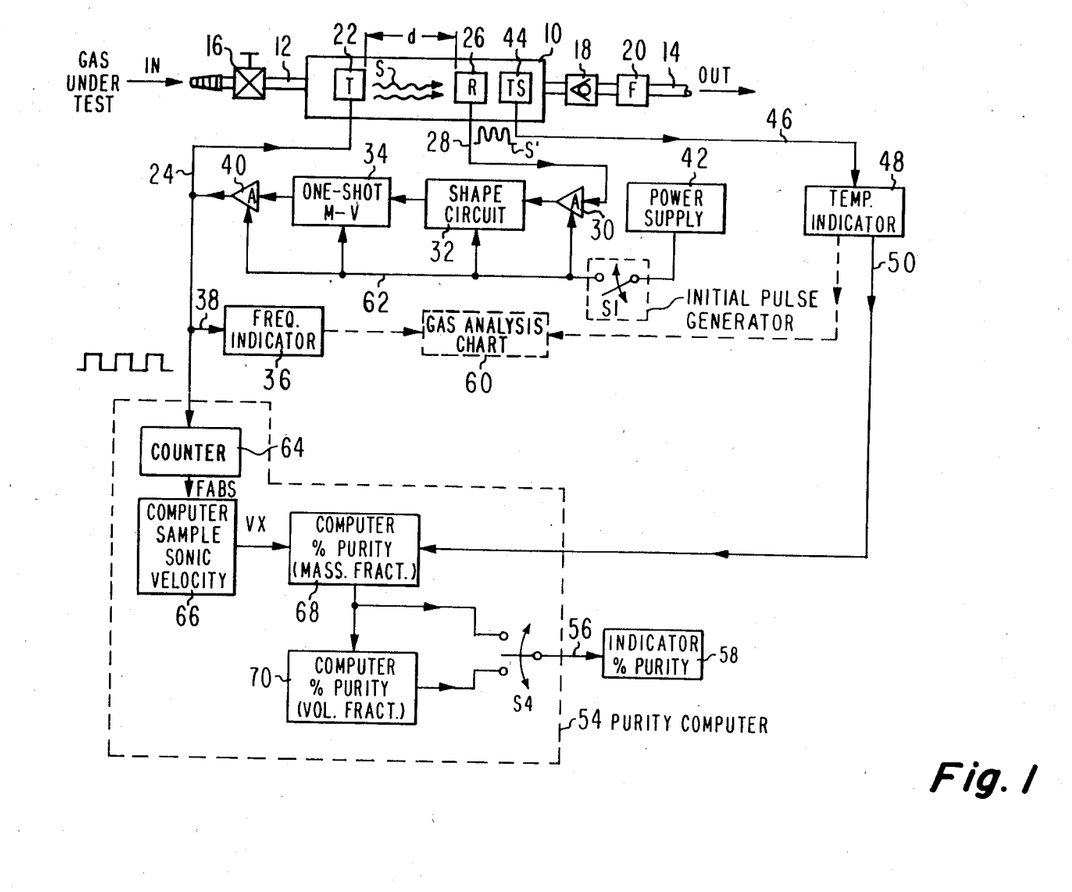
FIG. 1 is a partial schematic and partial block diagram illustrating one embodiment of the present invention.

A pulse regenerative embodiment is shown in FIG. 1, in which gas chamber 10 has a gas inlet port 12 and exhaust port 14. Valve 16 controls the inputting of gas into the chamber 10 via port 12. The exhaust port 14 includes a check valve 18 and a filter 20. Check valve 18 prevents entrance of ambient air through the exhaust port 14 into the chamber 10 and also controls the pressure of the gas within the chamber 10 to a desired pressure range. Filter 20 prevents entrance of airborne dirt which would tend to contaminate the check valve 18.

Located within chamber 10 is a sonic transmitting transducer 22. Transducer 22 may be a piezoelectric element which vibrates in response to an exciting signal supplied to it on input wire 24. The piezoelectric transducer 22 may be, for example, a 10 mil thick disc of piezoceramic material. A receiver 26 is located in the chamber 10 and spaced a distance d from the transmitting transducer 22. Receiver 26 may be any suitable device for receiving an acoustic signal S propagated by the transducer 22 in the gas under test in chamber 10. For example, receiver 26 may be a condensor electrode subminiature microphone.

The distance d is chosen so that the bandwidth requirements of the system are minimized and the resultant pulse repetition rate of the signal S is sufficiently low to be displayed on an electronic frequency counter 36 with a given desired resolution.

The receiver 26 generates an output pulse signal S' on output 28 in response to receipt of the incident pulse signal S. This output pulse signal S' is fed to an amplifier 30 which then supplies the amplified pulse to a pulse shaping circuit 32. Circuit 32 sharpens the pulses, i.e., narrows the signal in time by differentiation, base clips each pulse and provides its output pulse as an input to a one-shot multivibrator 34 of the required polarity to trigger multivibrator 34.

The pulse shaping circuit 32 is important because the output signal supplied to the multivibrator 34 should be free from interpulse disturbance. If this condition is not met, the circuit may oscillate as an ordinary feedback oscillator; and as long as there may be excess gain in the circuit, the frequency of the resultant pulses produced by the circuit will be more or less unstable. If the pulse train is substantially free of interpulse disturbances, the frequency of the regenerated pulses will be directly proportional to the transducer 22 spacing to receiver 26, distance d. The degree of sharpening the pulse and gain of the circuit is a function of the bandwidth (response) of the transducer 22 and receiver 26.

The output pulse of multivibrator 34 is amplified by power amplifier 40 which supplies the amplified pulse to the wire 24. The time duration of the multivibrator 34 generated signal pulse may be approximately 10 microseconds in one example employing a helium gas under test in which the spacing d is about 5.5 centimeters. In this example, the propagation delay of the pulse signal S may be approximately 55.6 microseconds.

In this case, the frequency indicator 36 may be a 4½-digit counter. It may be greater than a 4½-digit counter whose limiting frequency, in hertz, is beyond the frequency represented by pure helium at 50° C. when the distance d is 5.5 centimeters.

This circuit, operating correctly, will not start by itself. Therefore, the circuit includes an initial pulse generator comprising a switch S1 coupling power supply 42 to the amplifiers 30 and 40, pulse shaping circuit 32, and one-shot multivibrator 34. Switch S1 acts as an initial pulse generator by providing a contact spark of sufficient intensity to create an initial pulse to the system. In the alternative, an accessory transient generator (not shown), in addition to the switch S1, may be provided. Such an accessory transient generator may include a capacitor (not shown) to provide a capacitor generated pulse and operated by a separate panel mounted push button (not shown). In this case, switch S1 would be a type that would not generate the initial pulse.

Located within the chamber 10 is a temperature sensor 44 which may be a thermistor, a thermocouple, or precision resistance. The thermistor is preferred because of its smaller thermal inertia (faster response) and greater resolution as compared to the other devices. The temperature sensor 44 is mounted to sense the temperature of the gas within the chamber 10 and is thermally insulated from the chamber structure to provide an accurate measure of the gas temperature. Wire 46 connects temperature sensor 44 to the input of temperature indicator 48. Indicator 48 may be a panel meter of the LCD type which indicates temperature in degrees Celsius and may also provide a digital signal representing the measured temperature on output wire 50.

The regeneratively produced pulse signals on wire 24 are also coupled to input 52 of purity computer 54. The digital temperature indicating signal on wire 50 is supplied as another input to purity computer 54. The purity computer 54 computes the percent purity of the gas in chamber 10 and can do so as a mass fraction of the mixture or as a volume fraction of the mixture. The computed purity percentage is supplied as a signal on purity computer output 56 to the percent purity indicator 58 which provides an indication of that computed purity percentage.

In the case where it is desired to manually compute or manually determine the gas purity, a gas analysis chart 60 may be employed. Chart 60 is shown in phantom, since it is a look-up chart not electrically connected to the system. The chart 60 is employed to manually determine the gas purity based on the observed temperature indicated by indicator 48 and the observed propagation repetition rate of the signal S in the chamber 10 indicated by frequency indicator 36.

Figure 3:
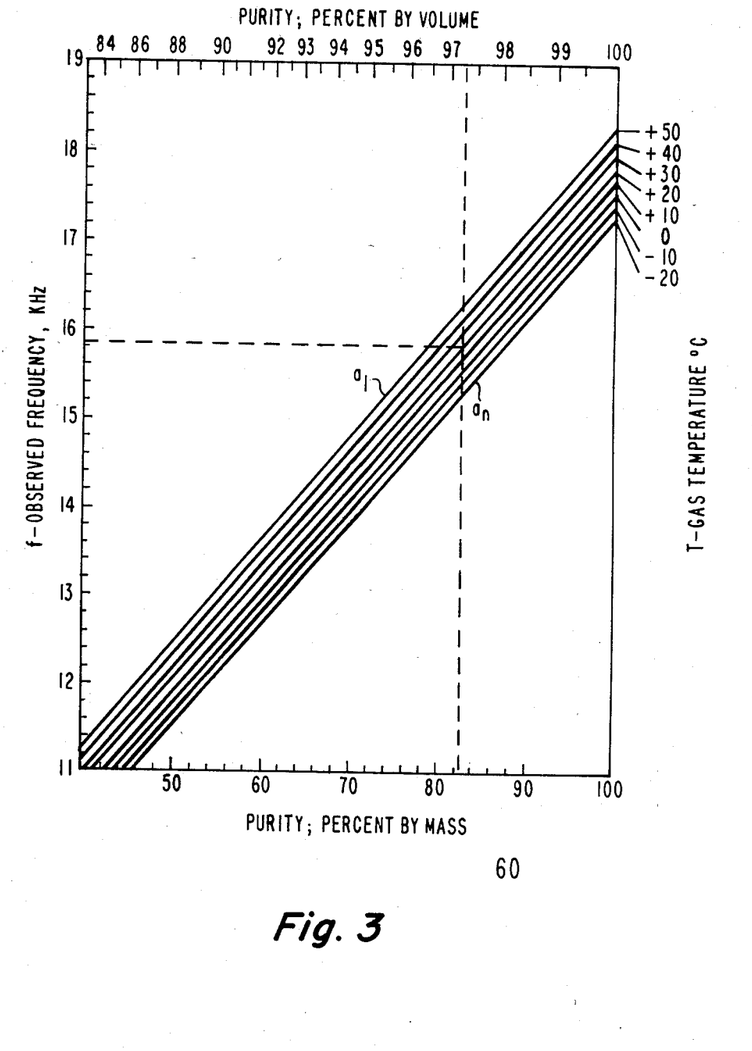
FIG. 3 is a chart used with the embodiments of FIGS. 1 and 2.

In FIG. 3, frequency f is shown as one coordinate of chart 60 and percent purity as the other. The purity coordinate may be presented as percent by volume and as percent by mass, as shown. A family of curves $a_1$-$a_n$ is shown, each representing the purity of a given gas at a given sensed temperature displayed by indicator 48. The chart is read by observing a particular curve $a_1$-$a_n$ for a given frequency and temperature and determining the percent purity therefrom. For example, the dashed lines illustrate a gas having an observed temperature of 20° C. and repetition rate f of 15.85 kilohertz (kHz). The percent by volume purity is read as 97.25% and the percent by mass purity is read as 83%. Other purities for anticipated nominal temperatures can be readily obtained from chart 60. This chart, for example, can represent a plot for helium gas employing a spacing distance d of 0.055 meters.

It is fundamental that the velocity of propagation of an acoustic wave in a gas is the product of frequency and wavelength.

$$V = f\lambda \tag{1}$$

Rearranging equation 1, produces equation 2:

$$f = V/\lambda \tag{2}$$

As shown in FIG. 1, the purity computer 54 includes a frequency counter 64 which counts the cycles of the detected output signal of amplifier 40, supplied on wire 24. The counter 64 provides a numerical value representing $F_{abs.}$, the absolute frequency or pulse repetition rate of the signal produced by the circuit of FIG. 1. The count representing the value of $F_{abs.}$ is supplied as an input to the sonic velocity computer 66. The computer 66 provides an output signal representing the value of $V_x$ which is the sonic velocity of the signal S in the gas under test in the chamber 10. It is known:

$$V_x = (F_{abs.})(D) \tag{3}$$

where D is the spacing d between the transducer 22 and the receiver 26 or the length of the path over which the signal S is propagated. The output signal $V_x$ produced by the velocity computer 66 is then applied as an input to the percent purity computer 68 for determining the mass fraction of the gas under test in the mixture. A second input of the percent purity computer 68 is the temperature indicating output signal of indicator 48.

The percent purity of the gas, for example, helium, as a mass fraction of mixture, ($P_{MH}$) is computed as follows:

$$P_{MH} = \frac{V_x - V_{CA}}{V_{CH} - V_{CA}} \tag{4}$$

where $V_{CA}$ and $V_{CH}$ represent sonic velocities in air and helium, respectively, corrected for the measured temperature as indicated by indicator 48. The term $V_{CH}$ can be computed as follows:

$$V_{CH} = V_{OH} + \Delta V_H \tag{5}$$

where $V_{OH}$ is the sonic velocity in helium at 0° C., and $\Delta V_H$ is the scalar increment of sonic velocity at the sensed temperature for helium. $\Delta V_H$ is computed as follows:

$$\Delta V_H = K_H \times T_x \tag{6}$$

where $K_H$ is the temperature coefficient of sonic velocity in helium and $T_x$ is the temperature of the gas mixture under test in degrees Celsius from indicator 48.

The sonic velocity in air, $V_{CA}$, is computed as follows:

$$V_{CA} = V_{OA} + \Delta V_A \qquad (7)$$

where $V_{OA}$ is the sonic velocity in air at 0° C., and $\Delta V_A$ is the scalar increment sonic velocity at the sensed temperature for air. $\Delta V_A$ is computed similarly as $\Delta V_H$ but using the appropriate temperature coefficient $K_A$ for air. Computation of $P_{MH}$ in the above equation (4) provides the percent purity of a gas under test as a mass fraction of the mixture. The $P_{MH}$ computer 68 output signal is supplied via switch S4 to indicator 58 for displaying the percent purity. These computations can be used also to create the chart 60 of FIG. 3.

The computation formed by the purity computer 54 is one which can be performed by a computer system including a programmed microprocessor including stored constants representing the values of D, $V_{OH}$, $V_{OA}$, $K_H$, and $K_A$ with the temperature from indicator 48 being supplied as one input and the signal on input 52 as a second input to the computer for performing the above calculations.

The output signal of the percent purity mass fraction computer 68 may also be supplied as an input to the percent purity volume fraction computer 70. The percent purity volume fraction computer 70 computes the purity of the gas under test as a volume fraction of the mixture by the following calculation:

$$P_{VH} = \frac{(P_{MH})(W_A)}{(P_{MH})(W_A) + W_H(100 - P_{MH})} \qquad (8)$$

where $P_{VH}$ is the percent purity of the gas under test as the volume fraction, $P_{MH}$ is the computed result of the percent purity mass fraction computer 68 $W_A$ and $W_H$ are input constants representing, respectively, molecular weights of the gas under test, i.e., air, and helium. The output of the percent purity as a volume fraction of the mixture 70 is supplied to a second terminal of switch S4 which can selectively couple either the computer 68 or computer 70 to the indicator 58 via line 56 for indicating the percent purity. The chart 60, FIG. 3, shows that the percent purity, percent by mass and percent by volume lie on the same coordinate and can be represented by a nomograph for mass-volume conversions.

Switch S4, which may be panel mounted, permits an operator to select either the mass or volume purity which may be displayed by indicator 58. The indicator 58 may be a numeric 3½-digit digital panel meter employing an LCD device which has good visibility in bright sunshine for field use.

An automatic system can automatically compute the percent purity of the gas under test in chamber 10 in response to the signal on wire 24 as an input to the purity computer 54. The computer 54 operates on the inputted regeneratively created pulse train and, in response to the measured temperature from indicator 48, computes percent purity and supplies a signal on output line 56 to indicator 58 which gives a visual indication of that percent purity. Accuracy of this system can be shown to be better than ±0.5%. The system requires no sophisticated circuits, relatively few components, and can be constructed of relatively portable elements for simplicity and easy field use by an inexperienced operator.

In operation of the system of FIG. 1, a gas under test is coupled to the valve 16 to supply gas to the chamber 10 via input port 12. A valve (not shown) may be on the output port 14 for controlling, in addition to the check valve 18, the pressure within the chamber 10 to a desirable level which may be slightly above atmospheric pressure, i.e., a positive pressure. That pressure level is to insure that the chamber 10 contains only the gas under test, i.e., gas bleeds through output port 14 to the ambient air to insure no small amount of ambient gas may leak back in through port 14. The system operates nominally at ambient pressure. In any case, the gas is supplied through the chamber 10 and bled through the output port 14 for a sufficient time to purge the chamber 10. The shape of the chamber 10 may be determined accordingly for achieving the greatest efficiency in this purging step, that is, purging the system in the least amount of time in the most reliable fashion. To this extent, the shape of the chamber 10 of FIG. 1 is merely schematic as the desired shape can be determined by one of ordinary skill.

Having purged the chamber 10, power supply 42 is coupled to the system by closing switch S1. Switch S1 is a type which when closed, causes a transient signal to be generated on the power supply output wire 62. This supplies power to the amplifier 30, pulse shaping circuit 32, the one-shot multivibrator 34, and the power amplifier 40. The resultant transient signal enters into the circuitry of the system to produce a square wave pulse on wire 24 and which is supplied as an input to transducer 22. The output of transducer 22 is an acoustic pulse signal S whose time duration is that of the multivibrator 34 output pulse. The receiver 26 receives the acoustic pulse after the propagation delay due to the time it takes the pulse to traverse the distance d. The receiver 26, in response to the received propagated acoustic pulse, produces pulse signal S' on output wire 28.

Signal S' is amplified by amplifier 30 and shaped by circuit 32 to trigger the one-shot multivibrator 34. The output pulse of multivibrator 34 is amplified by power amplifier 40 which provides a transducer 22 driving pulse. In response to that driving pulse, transducer 22 generates an additional acoustic pulse signal S which is received by receiver 26 and the process is repeated. This process regeneratively produces a pulse train whose pulses are at a certain pulse repetition rate. The pulse repetition rate of the set of resulting pulse signals is a function of the propagation velocity of the signal S over the distance d in the chamber 10. That is, the pulse train formed by signals S has a unique frequency which, for a given separation distance d, is a function of the gas mixture composition in chamber 10.

By way of example, employing a helium-air mixture as the gas under test, the percent of helium will determine the frequency of the pulse repetition rate of the resulting signal. The exemplary distance d spacing of 5.5 centimeters of transducer 22 from receiver 26 is arbitrary and may be set at any value in accordance with a given implementation.

The frequency indicator 36 indicates the pulse repetition rate of the resultant regeneratively generated pulse train signal. That pulse repetition rate may be computed by standard computation techniques into percent purity of the gas under test in this case, helium. In the alternative, the indication of frequency by indicator 36 and the temperature by indicator 48 may be used on chart 60, FIG. 3, as explained above to derive percent purity. The system of FIG. 1 can provide objective accuracy of the measurement of the percent purity of the gas, for example, helium, to an accuracy better than ±0.5% as readily observed in FIG. 3. Yet the circuitry of FIG. 1 is relatively simple, low cost, portable, and readily adaptable for field use.

Using helium as an example, an acoustic wave has a relatively high velocity in helium as compared to its velocity in air. For example, the propagation velocity of an acoustic wave in helium is 965 meters per second as compared to 331 meters per second in air. Of all gases, only hydrogen has a sonic velocity similar to that of helium. But, the amount of free hydrogen in air is so minute (one-half part per million, by volume) that its effect is negligible. By taking the weighted arithmetic mean of acoustic signal (sonic) velocities in principle air species according to their relative abundance in air, a sonic velocity can be obtained very close to the published value of the sonic velocity in air alone. Therefore, an instrument providing a measure of velocity of a sonic signal in a helium air mixture accurately represents the relative purity of helium alone.

There are also second order effects which should be considered. These effects are pressure, frequency, humidity, and temperature. By measuring the purity of the gas at nominally ambient pressure notwithstanding the slight positive pressure in the chamber 10, discussed above, the effect of pressure, therefore, is eliminated since barometric variations are relatively negligible with respect to absolute pressure. Scientific studies show that humidity also has a negligibly small affect on the velocity of an acoustic wave in a gas. Frequency and sound level are relatively inconsequential until thermodynamic effects are effective as a function of intensity. Phase disturbances may appear at very high frequencies. Studies relating sonic velocity as a function of temperature show that temperature is a problem which must be dealt with. As described above, temperature of the gas under analysis is considered in the disclosed embodiment and is employed in the computation of the percent purity. The temperature coefficients of the sonic velocities for air and helium are significant and thus need to be compensated for in providing an accurate measurement of percent purity.

Figure 2:
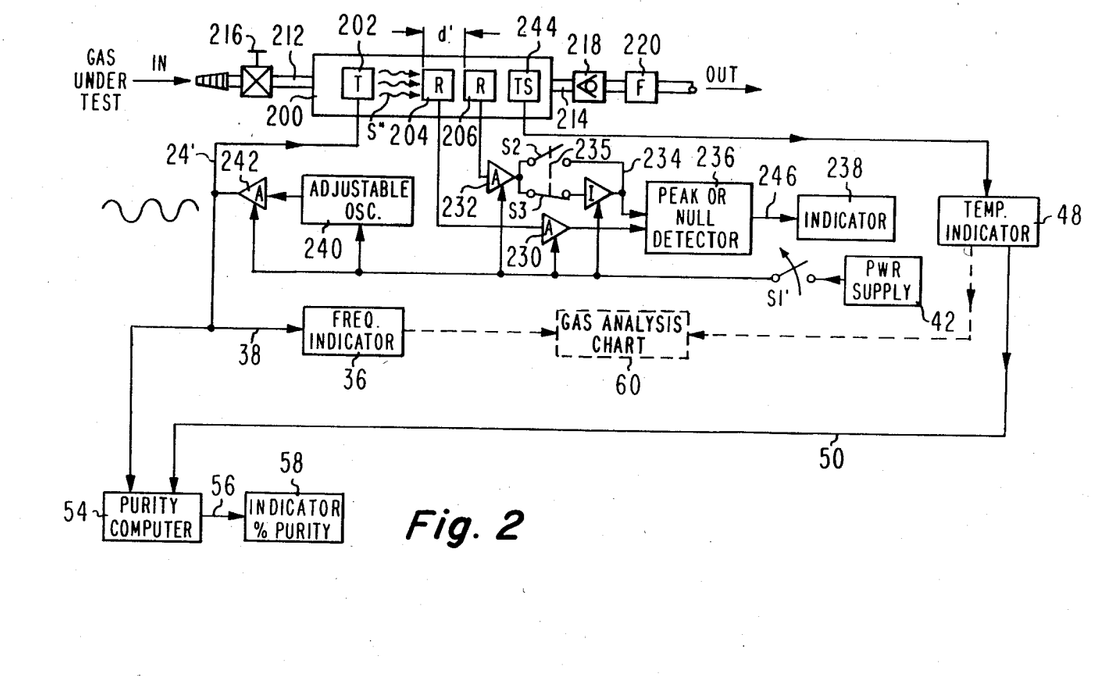
FIG. 2 is a partial schematic diagram and partial block diagram illustrating a second embodiment of the present invention.

In the alternative to the embodiment of FIG. 1, a second gas analysis system is shown in FIG. 2 and comprises a chamber 200, a transducer 202 in the chamber 200 for generating an acoustic signal, and two receivers 204 and 206. The receivers 204 and 206 are aligned along an axis with and downstream from the transducer 202 and have their receiving inputs spaced apart a distance d'. The chamber 200 has an input port 212 and a valve 216 for selectively supplying a gas under test to the chamber 200. The chamber 200 has an exhaust port 214 which exhausts the gas from chamber 200 to the ambient environment through check valve 218 and filter 220. Chamber 200 is functionally equivalent to the chamber 10 of the embodiment of FIG. 1 except for the two receiving microphones 204, 206.

Receivers 204 and 206 may be identical microphones. The transducer 202 may be a piezoelectric element for generating an acoustic signal, S", in response to an input electrical signal applied to the transducer 202. A temperature sensor 244 is in the chamber 200. The temperature sensor 244 is thermally isolated from the chamber 200 walls to provide an accurate indication of the temperature of the gas contained within the chamber 200. The output of receiving microphone 204 is applied as an input to amplifier 230 and the output of amplifier 230 is coupled as a first input to peak or null detector 236. The receiving microphone 206 is connected as an input to amplifier 232. The output of amplifier 232 is selectively applied through switch S3 as an input to an inverter 234 or through switch S2 as a second input to peak or null detector 236 on wire 237. The output of inverter 234 is applied on wire 237 as an alternative second input to peak or a null detector 236. Switches S2 and S3 are ganged as represented by the dashed line 235. The switches S2, S3 are in opposite states, one being closed and the other open. For example, S3 is shown closed and S2 open. When S3 is open, S2 is closed. This action, in the alternative, applies the output of amplifier 232 either directly to detector 236 or through the inverter 234 to detector 236.

Peak or null detector 236 may be a meter having a conventional moving coil and pointer configuration and need not be very accurate. The peak or null detector 236 can detect and indicate a null when the received signals produced by receivers 204 and 206 are in phase and one of those received signals is inverted by inverter 234. In this case, the outputs of inverter 234 and amplifier 230 are substantially equal in value and opposite in polarity so when algebraically summed, produce a null indication on detector 236. The two inverse signals which are in phase thus cancel one another and the peak or null detector provides a relatively accurate null or zero indication representing the in-phase condition.

For in-phase signals, the peak or null detector 236 can provide a peak indication by algebraically summing the outputs of amplifiers 232 and 230 without inversion. In a similar context, if the signals received by microphones 204, 206 are 180° out of phase, the outputs of amplifiers 230, 232 will cancel and produce a null on detector 236 when summed by the detector 236. If the output of amplifier 232 is inverted, then detector 236 sums the outputs and produces a peak signal on output 246.

An adjustable oscillator 240 has its output coupled as an input to power amplifier 242 whose output on wire 24' is supplied as an input to transducer 202 for driving the transducer 202. The oscillator 240 output is also coupled as an input to purity computer 54' via line 24' and as an input to frequency indicator 36 via input lead 38. The purity computer 54' produces the purity reading on indicator 58, as explained above in connection with FIG. 1. Oscillator 240 is a variable frequency sine wave device for providing an output signal at a selected frequency in the audio frequency range which may be, for example, 6–20 kHz. Power supply 42 supplies power to amplifiers 230, 232, 242, inverter 234, and oscillator 240 through switch S1'.

An operator adjusts the frequency of oscillator 240 for the lowest frequency that will produce a null or peak, as desired, on detector 236. The resultant selected frequency corresponds to a datum velocity of the propagated acoustic signal S" in the chamber 200 which is propagating between receivers 204 and 206 over the known distance d'.

The oscillator 240 may be adjusted manually or automatically. In the latter case (not shown), the oscillator frequency may be set by an AFC (automatic frequency control) loop which is driven by a null signal on the detector 236 output (not shown). In operation of the latter, the null signal on the output of detector 236 represents a signal of a certain value which is dithered until the null value is reached by the AFC loop referred above. To construct and design such an automatic circuit is within the skill of one of ordinary skill in the art.

The output of computer 54' is applied to percent purity indicator 58. Computer 54', FIG. 2, is the same computer as described above in connection with FIG. 1 except for counter 64. The counter 64, in this case, is responsive to the oscillations of the oscillating output signal of oscillator 240 rather than the pulses of such oscillating signals as occurs in the pulse train signal of the circuit of FIG. 1.

In operation of the system of FIG. 2, the oscillator 240 frequency output is manually or automatically adjusted so that the portions of the continuous acoustic signal S" in the chamber 200 produced by transducer 202 as detected by the receivers 204 and 206 are either in phase or 180° out of phase. The receiver outputs are supplied to the amplifiers 230 and 232, respectively. The outputs of the amplifiers are applied to the peak or null detector 236, as discussed, and indicator 238 thus indicates when the output of the detector 236 is a null or peak, i.e., the received signals are in phase, or 180° out of phase.

When a null or peak is indicated by indicator 238, the adjustment of oscillator 240 is halted. The frequency of the output signal of oscillator 240 at this time represents a measure of the percent purity (or composition by percent mass) of the gas within chamber 200. The oscillator 240 output is applied to purity computer 54' which computes the purity of the gas in chamber 200 as discussed above in connection with the system of FIG. 1.

The chambers 10 of FIG. 1 and 200 of FIG. 2 should be designed to minimize destructive acoustic reflections so that such reflections will not interfere with the primary signals S from transducer 22 or S" propagated from the transducer 202 to their corresponding receivers. Neither chamber, however, need be totally anechoic. The system of FIG. 1 is more tolerant of reflections than the system of FIG. 2 since the regenerating frequency has a natural tendency to reject lower level signals. This attribute may be considerably enhanced by judicious adjustment of the multivibrator 34, FIG. 1, threshold.

The pulse train or the sinusoidal signal of the respective embodiments of FIGS. 1 and 2, each has a unique frequency or repetition rate which, for a given sensor separation, is a function of the mixture composition (in the illustrative case employing helium, this is the percent of helium in the helium air mixture). The pulse train or the sine wave of unique frequency or repetition rate, serve as the basis for deriving the composition of the gas under test in the respective chambers 10 and 200 of the two systems utilizing stored constants which permit automatic computation of the desired purities. Such a computer system can be portable using microprocessors and employing the necessary computation programs stored in ROMs.

Because of the relatively low intensity of the acoustic wave, humidity and minority species of other gas constituents present in air have a negligible effect on the purity computation (approximate calculations can show that the effects of these other parameters may be in the order of 0.001% or less). Once having derived the velocity of the gas under test corrected for the prevailing temperature in the corresponding test chamber, the purity computation is relatively simple.

The mass purity computed by computer 68 can be conceived of as being linearly distributed since there is nothing beyond first order terms in the equations producing it. However, when the equivalent volume impurity values are juxtaposed to it, as in a nomograph, there is a relatively large expansion of the volume scale at the high end. This can be seen in FIG. 3 by observing the high end of the percent by volume scale. In the analysis of certain gases, for example, helium, for use in aerostat systems, it is desired to maintain a minimum of 95% purity wherein 90% purity can be seriously detrimental to the system. The resulting computation has an opened scale at the top end, as the scale approaches 100%, which provides not only greater resolution to the indicated calculation, but greater accuracy as compared to the mass fraction computation as can be observed by comparing the two scales of FIG. 3. For example, as shown, the 90 to 100% range of the volume purity extends over a range of about 55 to 100% for the mass fraction computation.

The arbitrary distance d or d' for the spacing of the transducers is at 5.5 centimeters with a $F_{abs.}$ in the 10 kHz-20 kHz range. These values provide a convenient compromise between chamber size and frequency limitations of sensitive transducers. Also the sequence 1.9999 is the limit of a 4½-digit digital display device which is convenient for the manual version of the instrument which provides a frequency indication from which an operator can compute temperature corrected percent purity using the chart of FIG. 3.

Thus, a system has been described which can, with high accuracy, simply and quickly analyze the percent purity of a gas, without using a reference gas or standard, without resorting to complex, costly phase analysis systems and which is convenient and portable. The described system derives the desired purity from the repetition rate of the oscillating audio signal propagating in the gas under test. The repetition rate is easily determined, as described, without resorting to unstable and unreliable standing waves created in a resonant system whose geometry is a significant factor of the system design or ambiguous and relatively unstable phase measurement techniques. While two exemplary embodiments have been described, other embodiments can be utilize in practicing the principles of the claimed invention.

What is claimed is:

1. A method of assaying the purity of a gas containing an unknown amount of contaminants comprising:
    propagating a sonic signal in the gas from a first point to a second point spaced a given distance from the first point, said signal having a repetition rate in a range of frequencies which is a function of the gas purity;
    sensing the temperature of said gas;
    determining the repetition rate of said signal at the second point;
    determining from said determined repetition rate and said given distance the velocity of the signal propagating between said two points; and
    deriving the purity of said gas from said determined velocity and said sensed temperature, said deriving step including computing the mass fraction of the gas-contaminant mixture ($P_{MG}$) where:

$$P_{MG} = \frac{V_x - V_{CA}}{V_{CG} - V_{CA}}$$

and where $V_x$ is said determined signal velocity computed from the determined frequency, and $V_{CG}$ represents the sonic velocity in the gas such that:

$$V_{CG} = V_{OG} + (K_G \cdot T_x)$$

where $V_{OG}$ is the sonic velocity in the gas at 0° C. and $K_G$ is the temperature coefficient of sonic velocity in the gas and $T_x$ is the sensed temperature, and, $V_{CA}$ represents the sonic velocity in an air such that:

$$V_{CA} = V_{OA} + (K_A \cdot T_x)$$

where $V_{OA}$ is the sonic velocity in air at 0° C. and $K_A$ is the sonic velocity temperature coefficient for air.

2. The method of claim 1 wherein said propagating step includes generating an audio signal pulse, propagating said audio signal pulse in said gas said given distance, sensing said propagated pulse after it traverses said pulse given distance, and repeating the above propagating steps in response to said sensing.

3. The method of claim 1 wherein said propagating step includes regeneratively propagating said signal in said gas; and wherein said repetition rate determining step includes measuring the regenerative repetition rate of said propagated signal.

4. The method of claim 1 wherein said deriving step includes indicating said derived purity as a percent purity.

5. The method of claim 1 wherein said propagating step includes generating an audio signal, propagating said audio signal in said gas from a first location; said repetition rate determining step includes sensing said propagated audio signal at second and third locations spaced from said first location to produce first and second respective oscillating signals having corresponding first and second respective phases at said second and third locations, and adjusting the frequency of said audio signal until said first and second sensed phases are in a given time coincidence; and said repetition rate determining step includes determining said adjusted frequency.

6. The method of claim 5 wherein said adjusting step includes adjusting said repetition rate of said generated signal until the sum of the amplitudes of the sensed first and second signals is a maximum.

7. The method of claim 5 wherein said adjusting step includes adjusting said repetition rate of said generated signal until the sum in the amplitudes of the sensed first and second signals is a minimum.

8. An apparatus for assaying the purity of a gas containing an unknown amount of contaminants comprising:
means for propagating a sonic signal in the gas from a first point to a second point spaced a given distance from the first point, said signal having a repetition rate in a range of frequencies which is a function of the gas purity;
means for sensing the temperature of said gas;
means responsive to said signal for determining said repetition rate at the second point and generating a signal representative of said determined repetition rate;
means responsive to said signal representative of said determined repetition rate for determining the velocity of said gas propagating between said two points and generating a signal representative of said determined velocity; and
means responsive to said signal representative of said determined velocity and said sensed temperature for deriving and displaying the purity of said gas, said means for deriving including means for computing the mass fraction of the gas-contaminant mixture ($P_{MG}$) where:

$$P_{MG} = \frac{V_x - V_{CA}}{V_{CG} - V_{CA}}$$

and where $V_x$ is said determined signal velocity computed from the determined frequency, and $V_{CG}$ represents the sonic velocity in the gas, such that:

$$V_{CG} = V_{OG} + (K_G \cdot T_x)$$

where $V_{OG}$ is the sonic velocity in the gas at 0° C. and $K_G$ is the temperature coefficient of sonic velocity in the gas and $T_x$ is the sensed temperature, and, $V_{CA}$ represents the sonic velocity in air such that:

$$V_{CA} = V_{OA} + (K_A \cdot T_x)$$

where $V_{OA}$ is the sonic velocity in air at 0° C., and $K_A$ is the sonic velocity temperature coefficient for air.

9. The apparatus of claim 8 wherein said means for propagating includes:
pulse generating means for generating an initial pulse;
transducer means responsive to said initial pulse for propagating a pulse signal in the audio frequency range the given distance in said gas;
receiver means for sensing the audio pulse signal after it traverses said given distance and for producing an output signal representing said sensed signal; and
means responsive to said output signal for repetitively regenerating subsequent audio pulses by said transducer, said subsequent pulses being generated at said repetition rate, said receiver means output signal comprising an electrical pulse, said regenerating means including means for shaping said electrical pulse to substantially remove interpulse disturbances and create a transducer means drive pulse from said shape electrical pulse.

10. The apparatus of claim 8 wherein said means for propagating includes:
means for generating an audio signal, and
transducer means for propagating said audio signal in said gas; and wherein
said means for determining the repetition rate includes:
first and second receiver means spaced from said transducer means and responsive to said generated audio signal for producing first and second respective oscillating signals having first and second respective phases corresponding to the relative spacing of said receiver means from said transducer means, and
means for adjusting the repetition rate of said generated oscillating signal until the first and second sensed phases occur in a given time coincidence.

11. Apparatus for assaying the purity of a gas comprising:
a chamber for containing said gas;
means for sensing the temperature of the gas in said chamber;
a transducer in said chamber for generating an audio signal pulse in response to an applied input signal;
a receiver in said chamber spaced a given distance from said transducer for generating an output signal in response to said audio signal pulse traversing said distance through said gas, the velocity of said audio signal pulse in said gas being a function of the purity of said gas;
means for applying said receiver output signal to said transducer to regeneratively produce a series of pulses having a repetition rate which is a function of the purity of said gas;
means for applying an initial input signal to said transducer to generate an initial audio signal in said chamber; and
means responsive to the repetition rate of said transducer means input signal and to the temperature sensed by the means for sensing for deriving the purity of said gas from said repetition rate and sensed temperature, said deriving step including computing the mass fraction of the gas-contaminant mixture ($P_{MG}$) where:

$$P_{MG} = \frac{V_x - V_{CA}}{V_{CG} - V_{CA}}$$

and where $V_x$ is said determined signal sonic velocity computed from the determined frequency, and $V_{CG}$ represents the sonic velocity in the gas such that:

$$V_{CG} = V_{OG} + (K_G \cdot T_x)$$

where $V_{OG}$ is the sonic velocity in the gas at 0° C. and $K_G$ is the temperature coefficient of sonic velocity in the gas and $T_x$ is the sensed temperature, and, $V_{CA}$ represents the sonic velocity in air such that:

$$V_{CA} = V_{OA} + (K_A \cdot T_x)$$

where $V_{OA}$ is the sonic velocity in air at 0° C. and $K_A$ is the sonic velocity temperature coefficient for air.

12. The apparatus of claim 11 wherein said means for deriving the purity includes means for automatically computing the percent purity of said gas.

13. The apparatus of claim 11 wherein said means for applying the receiver output signal to said transducer includes:
means for amplifying said receiver output signal, means responsive to said output signal for producing a first pulse of relatively short time duration,
means responsive to said first pulse for generating a second pulse of a given time duration; and
means for amplifying said second pulse and for applying said second pulse to said transducer to generate said audio signal of said given duration.

* * * * *

UNITED STATES PATENT AND TRADEMARK OFFICE
CERTIFICATE OF CORRECTION

PATENT NO. : 4,555,932
DATED : December 3, 1985
INVENTOR(S) : Edward Lewis Crosby, Jr.

It is certified that error appears in the above-identified patent and that said Letters Patent is hereby corrected as shown below:

Column 12, line 44, "utilize" should be --utilized--.

Column 13, line 22, delete "pulse".

Column 13, line 23, after "said" insert --pulse--.

Signed and Sealed this

Eleventh Day of February 1986

[SEAL]

Attest:

DONALD J. QUIGG

*Attesting Officer*  *Commissioner of Patents and Trademarks*